(12) United States Patent
Hirata et al.

(10) Patent No.: US 10,806,857 B2
(45) Date of Patent: Oct. 20, 2020

(54) FLUID CONTROL DEVICE

(71) Applicant: Murata Manufacturing Co., Ltd., Kyoto (JP)

(72) Inventors: Atsuhiko Hirata, Kyoto (JP); Yoshihide Amagai, Kyoto (JP); Nobuhiro Kondo, Kyoto (JP); Yoshitaka Hane, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 307 days.

(21) Appl. No.: 15/903,589

(22) Filed: Feb. 23, 2018

(65) Prior Publication Data

US 2018/0177942 A1 Jun. 28, 2018

Related U.S. Application Data

(63) Continuation of application No. PCT/JP2016/074577, filed on Aug. 24, 2016.

(30) Foreign Application Priority Data

Aug. 25, 2015 (JP) .................................. 2015-165544
May 28, 2016 (JP) .................................. 2016-106871

(51) Int. Cl.
*A61M 5/14* (2006.01)
*A61M 5/168* (2006.01)
(Continued)

(52) U.S. Cl.
CPC ...... *A61M 5/16804* (2013.01); *A61M 5/1411* (2013.01); *A61M 5/16877* (2013.01);
(Continued)

(58) Field of Classification Search
CPC ...... A61M 2205/14; A61M 2205/3306; A61M 39/28; A61M 39/281; A61M 5/1411;
(Continued)

(56) References Cited

U.S. PATENT DOCUMENTS 5,800,386 A * 9/1998 Bellifemine ........ A61M 39/281
604/65
6,491,659 B1 12/2002 Miyamoto
(Continued)

FOREIGN PATENT DOCUMENTS

| JP | H04-117267 U | 10/1992 |
|---|---|---|
| JP | 2002-336350 A | 11/2002 |
| JP | 2008-161610 A | 7/2008 |

OTHER PUBLICATIONS

International Search Report for International Application No. PCT/JP2016/074577, dated Oct. 4, 2016.
(Continued)

*Primary Examiner* — Rebecca E Eisenberg
(74) *Attorney, Agent, or Firm* — Pearne & Gordon LLP

(57) ABSTRACT

A fluid control device includes a tube insertion portion formed in a casing, a fixing member that fixedly holds, in the tube insertion portion, a tube inserted into the tube insertion portion, a pressing member driven by an actuator to press the tube within the tube insertion portion, and a controller that controls the actuator for the pressing member, wherein the controller controls the pressing member to start pressing on the tube after the fixing member has fixedly hold the tube in the tube insertion portion.

18 Claims, 13 Drawing Sheets

(51) Int. Cl.
*A61M 5/172* (2006.01)
*A61M 39/28* (2006.01)
(52) U.S. Cl.
CPC .......... *A61M 5/172* (2013.01); *A61M 39/281* (2013.01); *A61M 2205/14* (2013.01); *A61M 2205/3306* (2013.01); *A61M 2205/3561* (2013.01)
(58) Field of Classification Search
CPC .............. A61M 5/168; A61M 5/16804; A61M 5/16877; A61M 5/172
See application file for complete search history.

(56) References Cited

U.S. PATENT DOCUMENTS

| | | | |
|---|---|---|---|
| 6,558,347 B1* | 5/2003 | Jhuboo | A61M 5/14228 604/151 |
| 2010/0040481 A1* | 2/2010 | Wolff | A61M 5/14216 417/53 |
| 2013/0324975 A1* | 12/2013 | Douglas | A61M 39/22 604/544 |

OTHER PUBLICATIONS

Written Opinion for International Application No. PCT/JP2016/074577, dated Oct. 4, 2016.

\* cited by examiner

FLUID CONTROL DEVICE

This is a continuation of International Application No. PCT/JP2016/074577 filed on Aug. 24, 2016, which claims priority from Japanese Patent Application No. 2016-106871 filed on May 28, 2016 and from Japanese Patent Application No. 2015-165544 filed on Aug. 25, 2015. The contents of these applications are incorporated herein by reference in their entireties.

BACKGROUND

Technical Field

The present disclosure relates to a fluid control device that is attached to a tube through which a fluid flows, and that controls a flow rate of the fluid.

A drip set for a drip infusion generally includes an infusion tube through which a medical solution is fed from an infusion bag, a drip chamber enabling the medical solution in the infusion tube to be visually recognized, and a manual clamp for adjusting a flow rate of the medical solution flowing through the infusion tube. The manual clamp is disposed to grip the infusion tube from the outside, and adjusts the flow rate of the medical solution by controlling pressing strength applied to the infusion tube.

In the above-described drip set, an electrical clamp configured to control the pressing strength applied to the infusion tube with an actuator is used in some cases for automatic adjustment of the flow rate (see, e.g., Patent Document 1).

Patent Document 1: Japanese Unexamined Patent Application Publication No. 2008-161610

BRIEF SUMMARY

In the case of controlling the flow rate through the infusion tube with the electrical clamp, if the infusion tube is detached from the electrical clamp, there would be a risk that the flow rate through the infusion tube comes into a maximized state (called also a "free flow state") and the medical solution is infused excessively. Furthermore, combined use of the manual clamp and the electrical clamp may cause another risk that a medical staff mistakes operating procedures for the drip infusion and the infusion tube comes into the free flow state.

In consideration of the above-described problems, the present disclosure provides a fluid control device capable of reducing a risk that a tube is released from a pressed state and a flow rate is maximized in spite of being not intended by a medical staff.

The present disclosure provides a fluid control device including a tube insertion portion formed in a casing, a fixing member that fixedly holds, in the tube insertion portion, a tube inserted into the tube insertion portion, a pressing member driven by an actuator to press the tube within the tube insertion portion, and a controller that controls the actuator for the pressing member, wherein the controller controls the pressing member to start pressing on the tube after the fixing member has fixedly hold the tube in the tube insertion portion.

With the features described above, since the tube inserted into the tube insertion portion is fixedly held in the tube insertion portion by the fixing member, the tube is hard to displace from the tube insertion portion even with application of external force. Furthermore, since the tube inserted into the tube insertion portion is automatically pressed by the pressing member, the pressing on the tube is maintained unless an operation to stop the pressing is performed. As a result, a risk of the tube coming into the free flow state can be reduced.

The fixing member can be displaced between a tube fixing position at which the fixing member fixedly holds the tube in the tube insertion portion and a tube attaching/detaching position at which the fixing member allows the tube to be attached to and detached from the tube insertion portion, and the pressing member maintains the fixing member at the tube fixing position at least during a period in which the pressing member presses the tube.

With the features described above, during the period in which the pressing member presses the tube, the fixing member is restricted by the pressing member from moving to the tube attaching/detaching position. Accordingly, during the period in which the pressing member presses the tube, the tube cannot be removed from the tube insertion portion, and the risk of the tube coming into the free flow state can also be reduced from that point of view.

The above fluid control device can further include an operating member that receives an operation of displacing the fixing member from the tube fixing position to the tube attaching/detaching position, and a first resilient member that applies resilient force acting on the fixing member to displace the fixing member from the tube attaching/detaching position to the tube fixing position.

The above fluid control device can further include a second resilient member that applies resilient force acting on the operating member and the fixing member to attract both the members to each other.

With the features described above, the tube cannot be removed from the tube insertion portion unless the operating member receives the operation. Accordingly, unless a medical staff consciously operates the operating member, the tube cannot be removed from the tube insertion portion, and the risk of the tube coming into the free flow state can be further reduced from that point of view.

Moreover, the second resilient member is deformed even when the operating member receives the operation in a state where the fixing member is restricted by the pressing member from moving to the tube fixing position. It is hence possible to prevent the tube from being removed from the tube insertion portion with the fixing member moved forcedly, and to avoid damages of the fixing member, the operating member, the pressing member, the actuator, etc.

The above fluid control device further includes a drip unit in which a fluid flowing through the tube inserted into the tube insertion portion drips as drops, and a drop detector that detects an amount of the drops dripping in the drip unit. The controller may intensify or resume the pressing on the tube by the pressing member when the amount of the drops detected by the drop detector increases during an operation of reducing the pressing on the tube by the pressing member or after the pressing member and the tube have been moved away from each other.

In the fluid control device, the pressing on the tube by the pressing member needs to be stopped in order to remove the tube from the tube insertion portion. However, when the amount of the drops dripping in the drip unit increases (including an increase in the number of the drops and an increase in drop size) in a process where pressing strength applied to the tube by the pressing member gradually decreases during an operation of reducing the pressing on the tube by the pressing member or after the pressing member and the infusion tube have been moved away from each other, there is a risk that the tube may come into the free flow state if the pressing on the tube is stopped in such a state. The risk of the tube coming into the free flow state can be reduced by, as described above, intensifying or resuming the pressing on the tube when the amount of the drops dripping in the drop unit increases.

The casing can include a rolling element disposed at a position opposing to the fixing member in a sandwiching relation to a passage through which the tube is inserted into the tube insertion portion.

With the feature described above, even when the tube is caught between the fixing member and the rolling element in the tube insertion portion, the tube is movable to slide by the action of the rolling element. Therefore, the tube can be suppressed from being caught between the fixing member and the rolling element and from coming into an immovable state.

According to the present disclosure, since the tube inserted into the tube insertion portion is fixedly held by the fixing member and is pressed by the pressing member, it is possible to reduce the risk that the tube is released from a pressed state and a flow rate is maximized in spite of being not intended by a medical staff.

DETAILED DESCRIPTION

A fluid control device according to a first embodiment of the present disclosure will be described below in connection with the case where the fluid control device is applied to a drip set. In the following description, "up" and "down" are defined as denoting "up" and "down" in postures of individual components during drip infusion.

Figure 1:
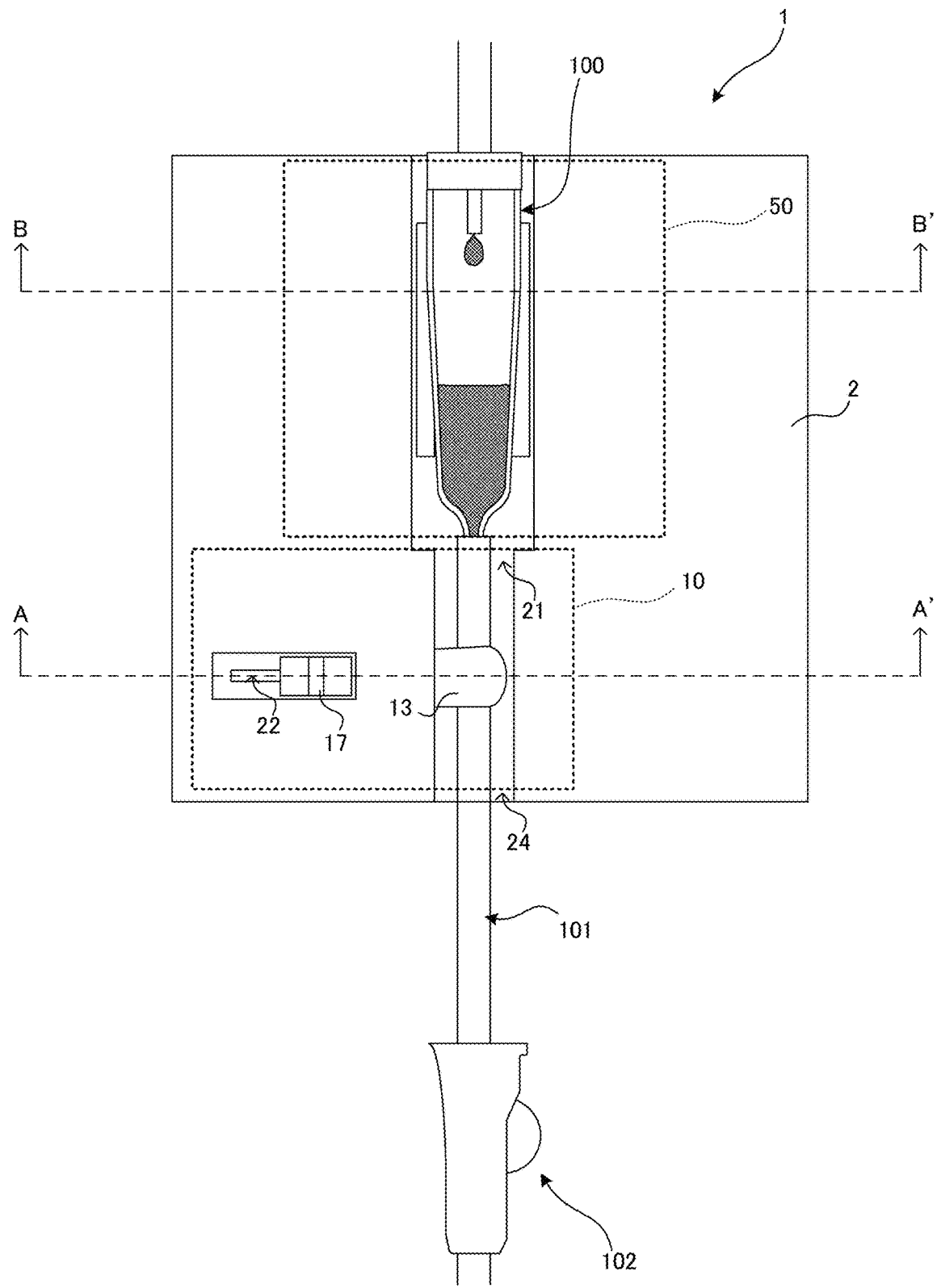
FIG. 1 is a schematic view of a drip set using a fluid control device according to a first embodiment of the present disclosure.

FIG. 1 is a schematic view of a drip set using a fluid control device 1 according to a first embodiment of the present disclosure. The fluid control device 1 illustrated in FIG. 1 constitutes part of a drip set and is used in combination with a drip chamber 100, an infusion tube 101, and a manual clamp 102.

Not-illustrated needles are attached to both ends of the infusion tube 101. The needle at the upper end side of the infusion tube 101 is pierced into a medical solution bag not illustrated. The needle at the lower end side of the infusion tube 101 is pierced, for example, into the skin of a patient not illustrated. The drip chamber 100 is disposed intermediate the infusion tube 101 at a position distanced ten and several cm to several ten cm from its upper end. The drip chamber 100 causes the medical solution flowing through the infusion tube 101 to drip in the form of drops. The medical staff can recognize a flowing state of the medical solution by checking the dripping of the medical solution in the drip chamber 100. The manual clamp 102 is attached to the infusion tube 101 at a position below the drip chamber 100. A portion of the infusion tube 101 above the manual clamp 102 and the drip chamber 100 are attached to the fluid control device 1.

The drip chamber 100 corresponds to one example of a drip unit in the present disclosure. The infusion tube 101 corresponds to one example of a tube in the present disclosure.

The fluid control device 1 includes a casing 2 and a not-illustrated operation panel. The operation panel includes various operation input units and a display unit. On the front side of the casing 2, there are disposed a drop detector 50 to which the drip chamber 100 is attached, and an electrical clamp 10 to which the infusion tube 101 is attached. The drop detector 50 captures the drops dripping in the drip chamber 100 with an optical sensor, such as a camera or a photosensor, and detects an amount of the drops on the basis of the number and sizes of the drops for the purpose of measuring a flow rate of the medical solution flowing through the infusion tube 101 per hour and an integrated flow rate from the start of the drip infusion. The electrical clamp 10 automatically adjusts pressing strength applied to the infusion tube 101 and adjusts the flow rate through the infusion tube 101 on the basis of the amount of the drops detected by the drop detector 50 such that the flow rate per hour and the integrated flow rate both preset by the medical staff are realized.

While the drop detector 50 and the electrical clamp 10 are disposed in one casing 2 in this embodiment, the drop detector 50 and the electrical clamp 10 may be disposed in different casings, and they may be connected to each other via a communication cable, for example.

Figure 2:
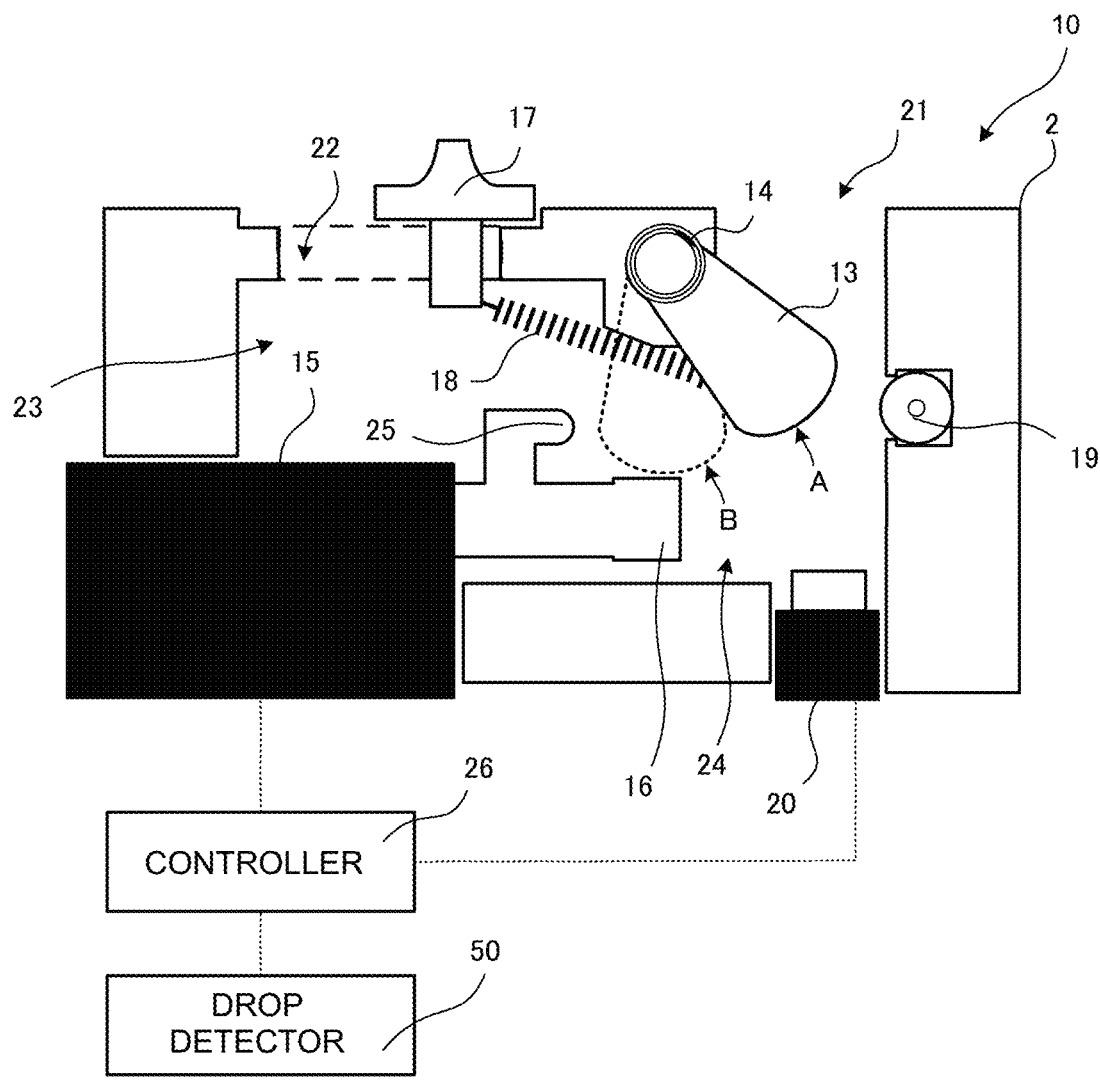
FIG. 2 is a schematic view illustrating a cross-section of an electrical clamp in the fluid control device according to the first embodiment of the present disclosure.

An exemplary detailed configuration of the electrical clamp 10 will be described below. FIG. 2 is a schematic view illustrating a cross-section of the electrical clamp 10, and it illustrates the cross-section passing a position denoted by a dotted line A-A' in FIG. 1. Members illustrated in FIG. 2 are not always needed to be all positioned on the same cross-section, and some of the members may be positioned apart from the cross-section illustrated in FIG. 2 in the up-down direction of the fluid control device 1 (direction perpendicular to the drawing sheet of FIG. 2).

The electrical clamp 10 includes the casing 2, a lever (fixing member) 13, a coil spring 14 (first resilient member), an actuator 15, a pressing member 16, a slider (operating member) 17, a tension spring (second resilient member) 18, a roller (rolling element) 19, a switch 20, and a controller 26.

The casing 2 has an opening 21, an opening 22, a casing chamber 23, and a tube insertion portion 24. The opening 21 is a slit formed in a front surface of the casing 2 while thoroughly extending in the up-down direction (see FIG. 1). The tube insertion portion 24 is a space defined on the inner side of the opening 21, and the infusion tube 101 is inserted into the tube insertion portion 24 through the opening 21. The opening 22 is a slit having ends and formed in the front surface of the casing 2 while extending in the left-right direction, and the slider 17 described later is attached to the opening 22 (see FIG. 1). The casing chamber 23 is a space defined on the inner side of the opening 22 and being adjacent to the tube insertion portion 24.

The lever 13 corresponds to a fixing member in the present disclosure. The lever 13 is displaced to be able to open and close the opening 21. More specifically, one end of the lever 13 is pivotally supported, at a position around the opening 21 on the side closer to the opening 22, by the casing 2 about a shaft extending along the up-down direction (see FIG. 1) of the casing 2. The other end of the lever 13 is positioned inside the opening 21 (i.e., on the side closer to the tube insertion portion 24) to be rotatable to open and close the opening 21. While the illustrated example represents the case of employing a lever as the fixing member, the fixing member may be another type having a different shape, such as a pin-shaped slider.

The coil spring 14 corresponds to a first resilient member in the present disclosure. The coil spring 14 is attached around the pivot shaft of the lever 13. The coil spring 14 is fastened at one end to the lever 13 and at the other end to the casing 2 in a state applying spring pressure between both the ends. Thus, the coil spring 14 biases the lever 13 to come closer to the opening 21. Accordingly, when no external force acts on the lever 13, the lever 13 takes a state rotated to the side where the opening 21 is closed, as denoted by a solid line in FIG. 2. Hereinafter, a position of the lever 13 in that state is called a tube fixing position A. Furthermore, when external force acts on the lever 13 in a predetermined rotation direction (clockwise in the illustrated example), the lever 13 takes a state rotated to the side where the opening 21 is opened, as denoted by a dotted line in FIG. 2. Hereinafter, a position of the lever 13 in that state is called a tube attaching/detaching position B. While the illustrated example represents the case of employing a coil spring as the first resilient member, the first resilient member may be a different type capable of biasing the fixing member with resiliency, such as a leaf spring or a rubber material.

The slider 17 corresponds to an operating member in the present disclosure, and receives an operation for rotating the lever 13 from the tube fixing position A to the tube attaching/detaching position B. The slider 17 is attached to the casing 2 to be slidable in the left-right direction along the opening 22. While the illustrated example represents the case of employing a slider as the operating member, the operating member may be a different type in the form of an appropriate switch, such as a button, rocker or toggle switch, insofar as being able to generate a displacement for switching. Moreover, while this embodiment represents an example in which an operation received by the operating member is mechanically transmitted to the lever 13 to operate the lever 13, the operating member may electromagnetically operate the lever 13 by employing another actuator different from the actuator 15.

The tension spring 18 corresponds to a second resilient member in the present disclosure. The tension spring 18 is laid for coupling between the slider 17 and the lever 13, and applies resilient force acting on the slider 17 and the lever 13 to attract them to each other. When the slider 17 is slid to the side near the lever 13, the tension spring 18 is in a state being almost not extended. Accordingly, in that state, the lever 13 is almost not attracted by the tension spring 18 and is held at the tube fixing position A by the coil spring 14. On the other hand, when the slider 17 is slid to the side away from the lever 13, the tension spring 18 is extended such that the force acting to attract the lever 13 exceeds the force applied from the coil spring 14 and acting to hold the lever 13 at the tube fixing position A. Thus, when the slider 17 is slid to the side farthest away from the lever 13, the lever 13 is attracted by the tension spring 18 and comes into a state rotated to the tube attaching/detaching position B.

The actuator 15 is disposed in the casing chamber 23. The actuator 15 is constituted by a stepping motor and a gear box, for example, and outputs a rotary motion of the stepping motor after conversion to a linear motion by the gear box.

The pressing member 16 is driven by the actuator 15 to take a state projecting into the tube insertion portion 24 or a state located away from the tube insertion portion 24. An amount by which the pressing member 16 projects into the tube insertion portion 24 is adjusted by the actuator 15. When the infusion tube 101 is arranged in the tube insertion portion 24, it is possible, by adjusting the projecting amount of the pressing member 16, to adjusts pressing strength laterally applied the infusion tube 101 by the pressing member 16, and to control the flow speed and the flow rate of the medical solution flowing through the infusion tube 101.

A stopper 25 is integrally molded on the pressing member 16. When the pressing member 16 is in the state not projecting into the tube insertion portion 24, the stopper 25 is positioned on the side closer to the casing chamber 23 than a region where the lever 13 is rotated. When the pressing member 16 is in the state projecting into the tube insertion portion 24, the stopper 25 is positioned in an overlapped relation to the tube attaching/detaching position B. Thus, in the state of the pressing member 16 projecting into the tube insertion portion 24, when the lever 13 is forced to rotate from the tube fixing position A toward the tube attaching/detaching position B, the rotation of the lever 13 is restricted and the lever 13 is maintained at the tube fixing position A because the lever 13 interferes with the stopper 25 positioned at the tube attaching/detaching position B.

The roller 19 is mounted to the casing 2 at a position opposing to the lever 13 with the opening 21 interposed therebetween. The roller 19 is rotatable about a shaft extending parallel to the pivot shaft of the lever 13. With the provision of the roller 19, even if the infusion tube 101 is caught between the lever 13 and a wall surface of the casing 2 when the infusion tube 101 is inserted into the tube insertion portion 24, the infusion tube 101 is more apt to slide by the action of the roller 19. It is hence possible to avoid an event that the infusion tube 101 is collapsed (or bitten) by the lever 13 and it cannot be inserted into the tube insertion portion 24. The roller 19 and the lever 13 can be made of a low-friction material having good slidability, such as a fluorine resin or polyacetal, to ensure smoother sliding of the infusion tube 101.

The switch 20 includes a push button portion positioned in the tube insertion portion 24, and detects the infusion tube 101 in a state fixedly held in the tube insertion portion 24 upon the push button portion being pressed by the infusion tube 101. Instead of the switch 20, a pressure sensor, an infrared sensor, or another type of switch may be used to detect the infusion tube 101 in the state fixedly held in the tube insertion portion 24.

The controller 26 controls the entirety of the fluid control device 1, namely the operation panel, the drop detector 50, and the electrical clamp 10. The controller 26 controls the actuator 15 for the electrical clamp 10 on the basis of the amount of the drops detected by the drop detector 50 and the state of the switch 20.

Detailed operations and control of the electrical clamp 10 will be described below in accordance with the operating procedures when the medical staff performs the drip infusion using the fluid control device 1.

At the start, the medical staff performs drip preparation work. The drip preparation work is to set the drip set into the state illustrated in FIG. 1.

The medical staff performing the drip preparation work first closes the manual clamp 102 and pierces the needle at the upper end side of the infusion tube 101 into the medical solution bag. Then, the medical staff performs priming work, etc. by pressing the drip chamber 100 and feeding the medical solution to the drip chamber 100. After the priming work, the medical staff attaches the drip chamber 100 and the infusion tube 101 to the drop detector 50 and the electrical clamp 10 of the fluid control device 1.

Figure 3A:
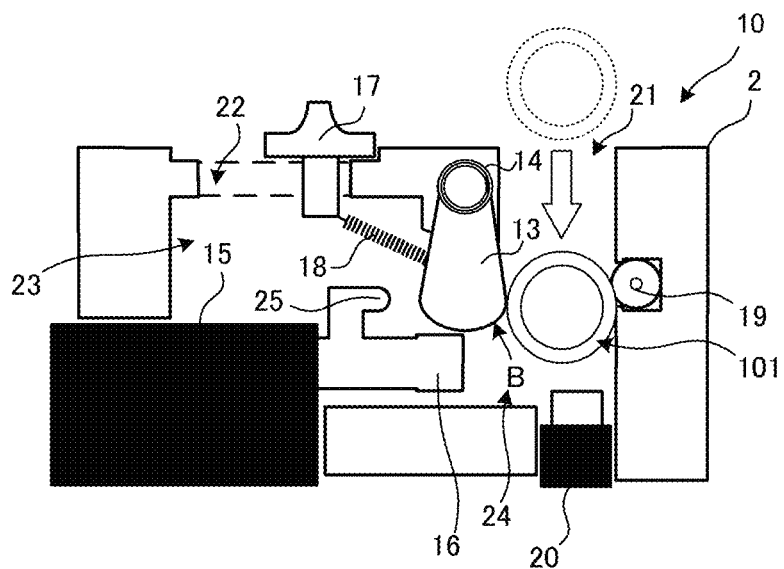
FIGS. 3A, 3B and 3C are each, a schematic view illustrating operations of individual components when a tube is attached to the electrical clamp in the fluid control device according to the first embodiment of the present disclosure.
Figure 3B:
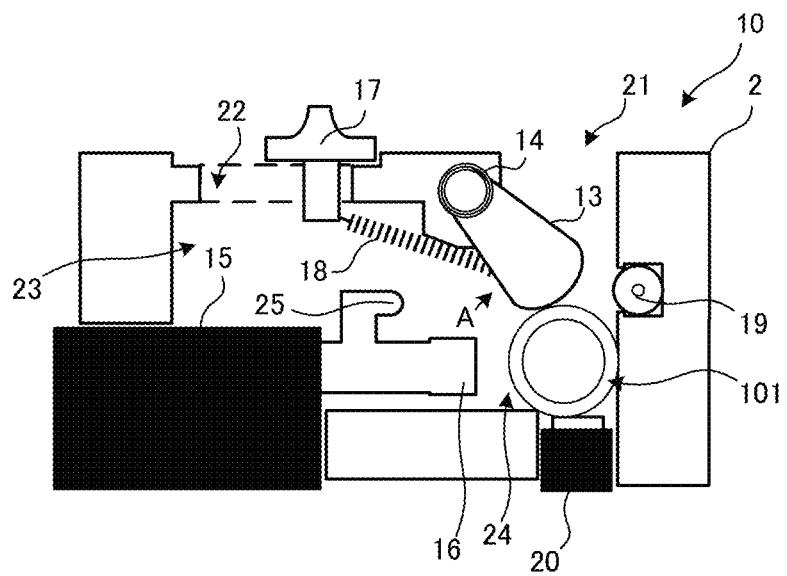
Figure 3C:
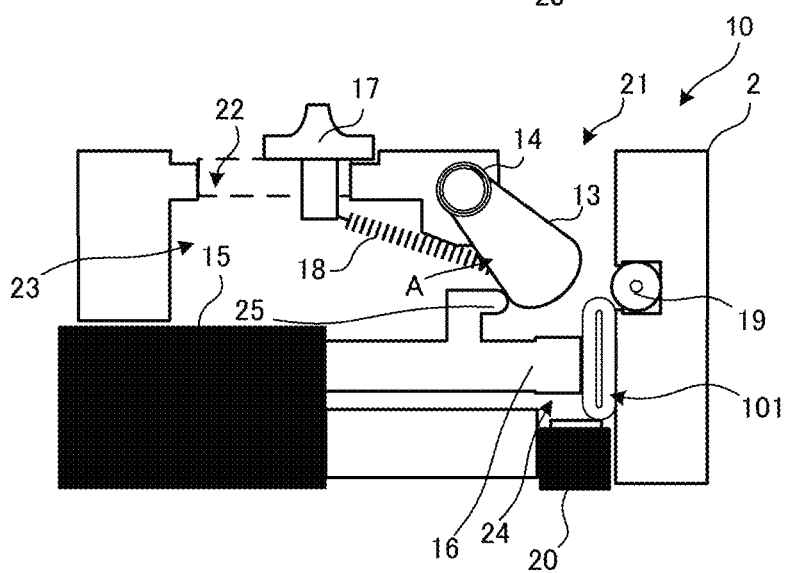

FIGS. 3A-3C are schematic views illustrating operations of individual components of the electrical clamp 10 when the infusion tube 101 is attached to the electrical clamp 10.

The medical staff pushes the infusion tube 101 into the opening 21 of the electrical clamp 10. The infusion tube 101 is pushed against the lever 13, whereupon the lever 13 is rotated from the tube fixing position A to the tube attaching/detaching position B by pressure applied from the infusion tube 101, as illustrated in FIG. 3A. At that time, the coil spring 14 is deformed to be further twisted. The tension spring 18 is deformed to lose its extension and to sag.

When the medical staff further pushes the infusion tube 101 into the tube insertion portion 24, the coil spring 14 is deformed to restore from the twisted state. The tension spring 18 is deformed to extend slightly. Hence the lever 13 is rotated to return from the tube attaching/detaching position B to the tube fixing position A.

On that occasion, when the infusion tube 101 is pushed to be positioned closer to the tube insertion portion 24 than a position where a tip end of the lever 13 in the tube attaching/detaching position B and the roller 19 are opposed to each other, the roller 19 and the lever 13 come into contact with the infusion tube 101 at a semicircular portion on the side pushed by the medical staff, as illustrated in FIGS. 3A and 3B. With the rotation of the lever 13, the infusion tube 101 is fully pushed into the tube insertion portion 24. As a result, the infusion tube 101 is inserted into the tube insertion portion 24 and is fixedly held in the tube insertion portion 24 by the lever 13 having returned to the tube fixing position A.

Thus, since the infusion tube 101 is fixedly held in the tube insertion portion 24 by the lever 13, the infusion tube 101 can be avoided from being displaced from the tube insertion portion 24 even when the infusion tube 101 is strongly pulled by external force during drip infusion performed later. According to the fluid control device 1, therefore, even when the infusion tube 101 is strongly pulled by external force, a risk of the infusion tube 101 coming into the free flow state during the drip infusion is low, and the drip infusion can be performed safely.

Furthermore, when the infusion tube 101 is fixedly held in the tube insertion portion 24, the button portion of the switch 20 is pushed upon the infusion tube 101 contacting the switch 20. In response, the controller 26 (see FIG. 2) controls the actuator 15 to project the pressing member 16 into the tube insertion portion 24. Accordingly, as illustrated in FIG. 3C, the pressing member 16 having been so far positioned on the side closer to the casing chamber is projected into the tube insertion portion 24, and the infusion tube 101 fixedly held in the tube insertion portion 24 is pressed laterally. Although a degree at which the infusion tube 101 is collapsed is not particularly limited, the illustrated example represents the case where the pressing member 16 is projected into the tube insertion portion 24 to such an extent that the infusion tube 101 is almost completely collapsed and closed under pressure (namely, a state where an opening degree is substantially zero).

In the fluid control device 1, after the infusion tube 101 is attached to the electrical clamp 10 by the medical staff, the electrical clamp 10 automatically presses and closes the infusion tube 101. Accordingly, the operating procedures to be performed by the medical staff are relatively simple, and a risk of the infusion tube 101 coming into the free flow state is very low even when the medical staff attaches the infusion tube 101 to the electrical clamp 10 and then immediately opens the manual clamp 102.

After the above-described drip preparation work, the medical staff performs drip starting work. In the drip starting work, the medical staff operates, for example, the operation panel of the fluid control device 1 to start the drip infusion.

Figure 4:
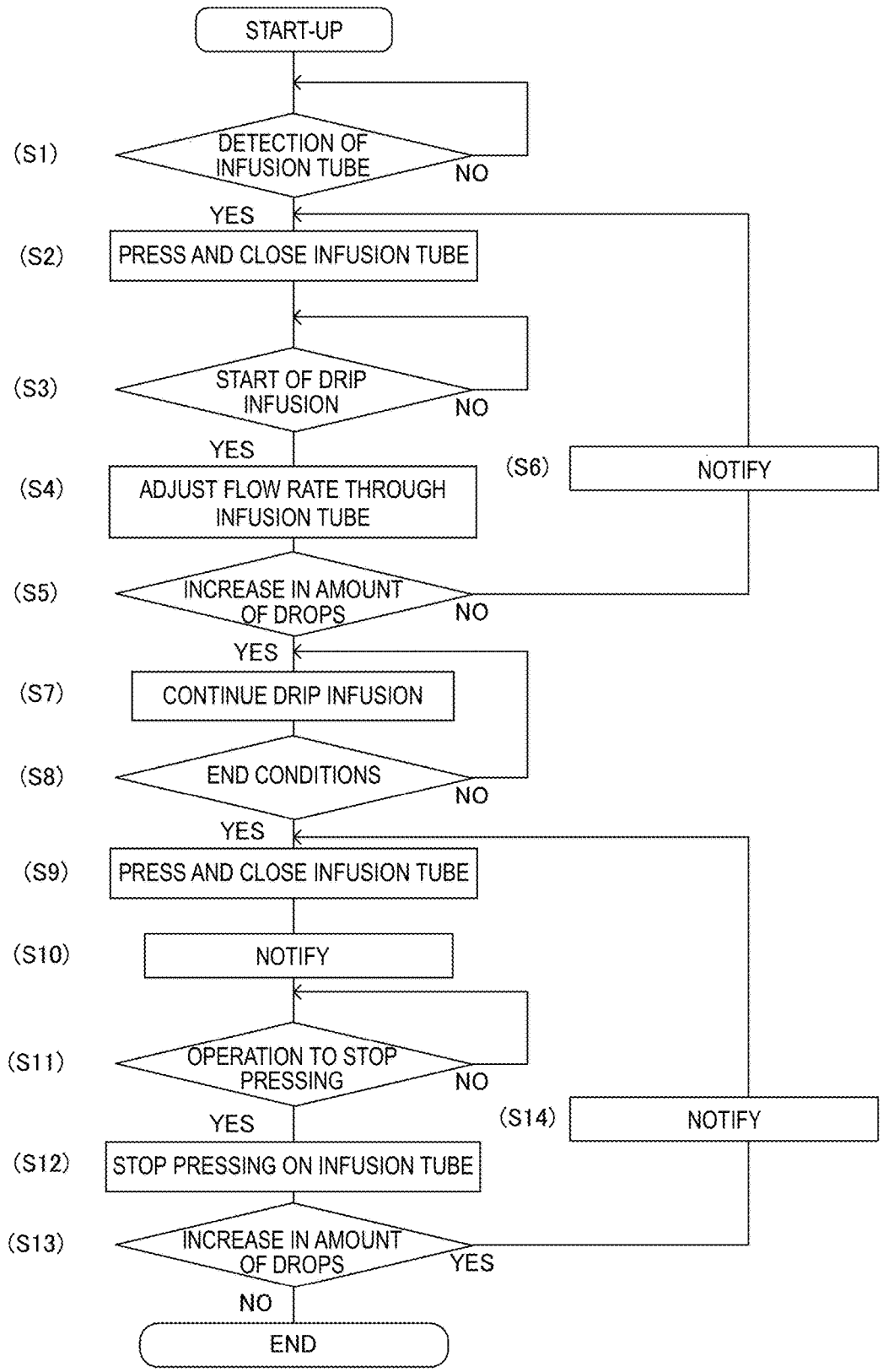
FIG. 4 illustrates one example of control flow in the fluid control device according to the first embodiment of the present disclosure.

FIG. 4 illustrates one example of control flow executed by the controller 26.

The controller 26 is started up in a stage of the above-described drip preparation work, and it waits until the switch 20 detects the infusion tube 101 (S1). If the switch 20 detects the infusion tube 101, the controller 26 controls the actuator 15 to press and close the infusion tube 101 by the pressing member 16 (S2).

Then, the controller 26 waits until the start of the drip infusion is instructed with an operation made on, for example, the operation panel (S3). Upon the start of the drip infusion being instructed, in order to satisfy operating conditions, such as the flow rate per hour, preset by the medical staff, the controller 26 controls the actuator 15 and performs initial adjustment of the flow rate and the pressing strength applied to the infusion tube 101 by the pressing member 16 (S4).

However, if the amount of the drops detected by the drop detector 50 does not increase immediately after the start of the drip infusion, the controller 26 regards the event as indicating that the medical staff forgets to open the manual clamp 102, and outputs, to the display unit, a notification signal for warning that there is no increase in the flow rate (S5→S6). Thereafter, the controller 26 controls the actuator 15 to press and close the infusion tube 101 again, and then waits again until the start of the drip infusion is instructed (S2→S3).

If the amount of the drops detected by the drop detector 50 properly increases immediately after the start of the drip infusion, the controller 26 continues the drip infusion while controlling the actuator 15 on the basis of the amount of the drops detected by the drop detector 50 (S7).

If drip ending conditions are satisfied upon an accumulated dripping time and an accumulated flow rate reaching values preset by the medical staff, the controller 26 controls the actuator 15 to press and close the infusion tube 101 (S8→S9). At that time, the controller 26 may adjust the actuator 15 to provide a small flow rate for a certain time instead of pressing the infusion tube 101 into the completely closed state. This is effective in preventing a blood clot from being formed in an infusion path. Thereafter, the controller 26 outputs, to the display unit, a notification signal for notifying the end of the drip infusion (S10).

If the drip infusion is ended as described above, the medical staff performs drip ending work. In the drip ending work, the medical staff closes the manual clamp 102 and then removes the infusion tube 101 from the fluid control device 1.

Figure 5A:
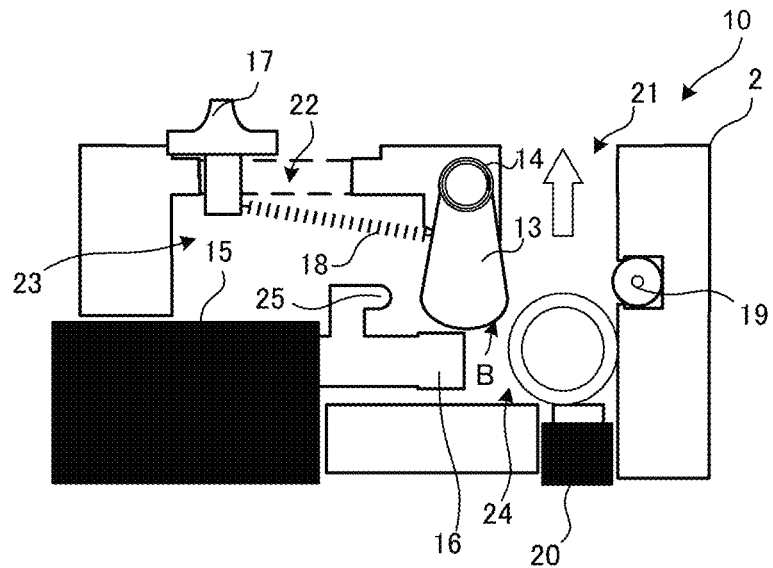
FIGS. 5A and 5B are each, a schematic view illustrating operations of the individual components when the tube is detached from the electrical clamp in the fluid control device according to the first embodiment of the present disclosure.

FIG. 5A is a schematic view referenced to explain operations of the individual components of the electrical clamp 10 when the infusion tube 101 is detached from the electrical clamp 10. On that occasion, the medical staff operates, for example, the operation panel to stop the pressing on the infusion tube 101 by the pressing member 16. Then, the medical staff operates the slider 17 to displace the lever 13 from the tube fixing position A to the tube attaching/detaching position B. Through the operating procedures described above, the infusion tube 101 can be removed from the tube insertion portion 24.

More specifically, as illustrated in FIG. 4, the controller 26 waits until the stop of the pressing on the infusion tube 101 by the pressing member 16 is instructed, for example, with an operation made on the operation panel (S11). Upon the stop of the pressing on the infusion tube 101 being instructed, the controller 26 controls the actuator 15 to move the pressing member 16 away from the tube insertion portion 24, and to stop the pressing on the infusion tube 101 (S12). Hence the stopper 25 integrally provided on the pressing member 16 is also moved away from the tube attaching/detaching position B. Accordingly, the lever 13 can be displaced from the tube fixing position A to the tube attaching/detaching position B by operating the slider 17.

However, if the amount of the drops measured by the drop detector 50 increases immediately after the pressing member 16 has started to move away from the tube insertion portion 24, there may be a risk that the medical staff forgets to close the manual clamp 102. More specifically, if the manual clamp 102 is in the open state in the process where the pressing member 16 is moved away from the tube insertion portion 24, the dripping of the medical solution in the drip chamber 100 gradually increases. This may lead to a risk that the infusion tube 101 comes into the free flow state if the pressing member 16 is continuously moved away from the tube insertion portion 24 in such a state. In consideration of the above point, if the amount of the drops measured by the drop detector 50 increases (S13: YES), the controller 26 makes control to press and close the infusion tube 101 again (S9). Stated in another way, if the amount of the drops detected by the drop detector 50 increases (S13: YES) during the operation of reducing the pressing on the infusion tube 101 by the pressing member 16, or after the pressing member 16 and the infusion tube 101 have been moved away from each other, the controller 26 intensifies or resumes the pressing on the infusion tube 101 by the pressing member 16 (S9).

The controller 26 outputs, to the display unit, a notification signal for warning that there is an increase in the amount of the drops (S10), and then waits again until the stop of the pressing is instructed (S11).

If the infusion tube 101 comes into the free flow state, there would be a risk that the medical solution comes into a continuously existing state in the drip chamber 100, and the optical drop sensor is hard to detect the drops. In consideration of the above point, the operation of stopping the pressing on the infusion tube 101 by the pressing member 16 can be moderately performed to such an extent that three seconds or longer takes until the pressing member 16 departs away from the tube insertion portion. This enables the manual clamp 102 being in the open state to be detected with high reliability in the process where the pressing member 16 is moved away from the tube insertion portion 24.

When the medical staff performs the proper procedures of closing the manual clamp 102 and then operating the operation panel to move the pressing member 16 away from the tube insertion portion 24, the medical solution does no longer drip in the drip chamber 100, or drips in very small amount, such as just one drop, even if so. Accordingly, the increase in the amount of the drops can be determined in a manner of setting a certain threshold for the amount of the drops, and determining that the amount of the drops has increased when the detected amount exceeds the threshold.

Figure 5B:
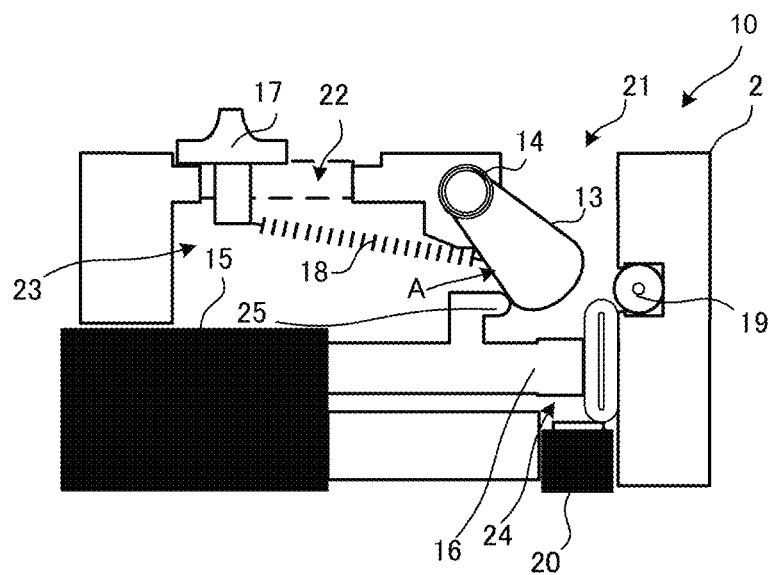

FIG. 5B is a schematic view illustrating operations of the individual components when the medical staff is going to operate the slider 17 and to detach the infusion tube 101 from the tube insertion portion 24 while forgetting the operation of stopping the pressing on the infusion tube 101 by the pressing member 16.

In the above case, because the pressing member 16 is projected into the tube insertion portion 24, the stopper 25 integrally molded on the pressing member 16 is in overlapping relation to the tube attaching/detaching position B of the lever 13. Therefore, the lever 13 cannot be rotated from the tube fixing position A to the tube attaching/detaching position B, and the infusion tube 101 cannot be removed from the tube insertion portion 24.

On that occasion, no matter how much the medical staff tries to operate the slider 17, the tension spring 18 is deformed just to extend idly, and it is difficult to displace the lever 13 from the tube fixing position A to the tube attaching/detaching position B. Thus, with the provision of the tension spring 18 laid for coupling between the lever 13 and the slider 17, excessive force can be avoided from acting on the lever 13 and the slider 17 to cause breakdown, and the lever 13 can be prevented from being forcedly moved and from damaging the pressing member 16 and the actuator 15.

As described above, when the medical staff engaged in the drip infusion using the fluid control device 1 is going to remove the infusion tube 101 from the tube insertion portion 24, the medical staff is needed to consciously release the infusion tube 101 from the pressed state, and then to move the lever 13 by operating the slider 17. Accordingly, a false operation of erroneously removing the infusion tube 101 from the tube insertion portion 24 during the drip infusion can be prevented. Thus, by performing the drip infusion with the fluid control device 1, it is possible to reduce the risk of the infusion tube 101 coming into the free flow state, and to safely perform the drip infusion.

A fluid control device according to a second embodiment of the present disclosure will be described below. The following description is made mainly about features of the second embodiment while components having similar configurations and substantially the same functions to those in the first embodiment are denoted by the same reference signs and description of those components is omitted.

The fluid control device according to the second embodiment includes an electrical clamp 10E.

Figure 6:
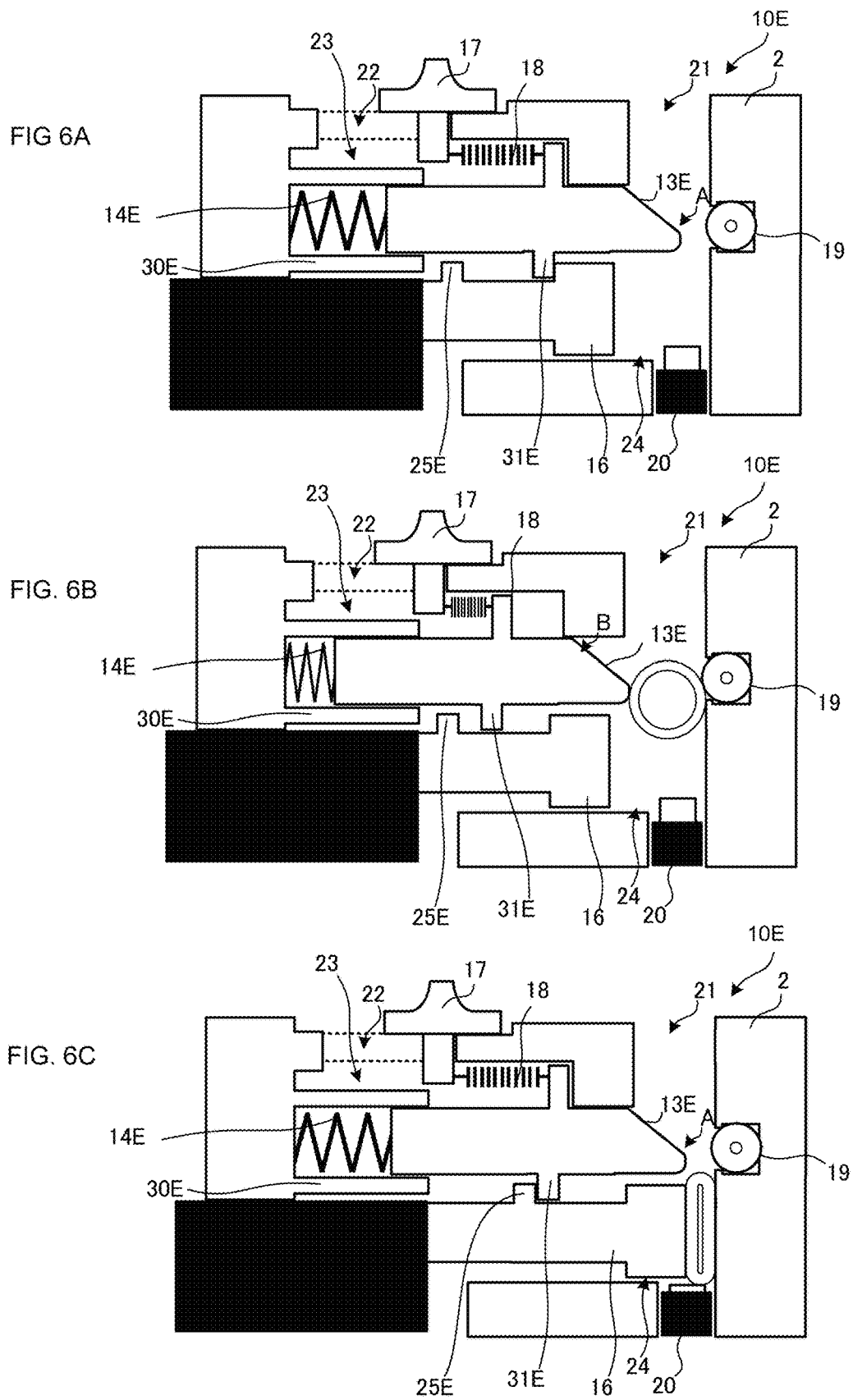
FIGS. 6A, 6B and 6C are each, a schematic view illustrating operations of individual components when a tube is attached to an electrical clamp in a fluid control device according to a second embodiment of the present disclosure.

FIGS. 6A-6C are schematic views illustrating a cross-section of the electrical clamp 10E.

The electrical clamp 10E includes a casing 2, a plunger (fixing member) 13E, a compression spring (first resilient member) 14E, an actuator 15, a pressing member 16, a slider (operating member) 17, a tension spring (second resilient member) 18, a roller (rolling element) 19, a switch 20, and a not-illustrated controller 26.

The plunger 13E corresponds to the fixing member in the present disclosure. One end portion of the plunger 13E is reciprocally movable, as with the pressing member 16, between a state retracted into a casing chamber 23 and a state projecting into a tube insertion portion 24. The other end of the plunger 13E is attached to the compression spring 14E and is fixedly fitted, together with the compression spring 14E, to a plunger fixing portion 30E provided in the casing 2. The compression spring 14E corresponds to the first resilient member in the present disclosure, and biases the plunger 13E toward the tube insertion portion 24. As illustrated in FIG. 6B, when the infusion tube 101 is pushed into the tube insertion portion 24, external force acts on the plunger 13E from the infusion tube 101 to push the plunger 13E toward the casing chamber 23, whereby the plunger 13E is moved toward the casing chamber 23 away from the tube insertion portion 24. At that time, the compression spring 14E is compressed. Furthermore, as illustrated in FIG. 6C, when the infusion tube 101 is inserted to a position closer to the tube insertion portion 24 than the tube fixing position A of the plunger 13E, the external force is no longer applied to the plunger 13E, and the plunger 13E is projected into the tube insertion portion 24 by being biased by the compression spring 14E. Thus, the infusion tube 101 is fixedly held in the tube insertion portion 24 by the plunger 13E. In such a state, the actuator 15 is driven by the not-illustrated controller 26 such that the pressing member 16 is projected into the tube insertion portion 24 to press and close the infusion tube 101.

Moreover, the pressing member 16 includes a stopper 25E, and the plunger 13E includes a bumping portion 31E. As illustrated in FIG. 6C, when the pressing member 16 is in the state projecting into the tube insertion portion 24, the stopper 25E is positioned oppositely close to or in contact with the bumping portion 31E of the plunger 13E in the tube fixing position A, thereby restricting the plunger 13E from returning to the tube attaching/detaching position B from the tube fixing position A and maintaining the plunger 13E at the tube fixing position A.

In the present disclosure, the fixing member may be constituted by a reciprocating plunger as in the electrical clamp 10E in this embodiment. The fixing member in the present disclosure is just needed to be able to fixedly hold at least the tube in the tube insertion portion 24, and it may have any suitable shape in practice. The actuator 15 and the stopper 25E may also have any suitable shapes in practice insofar as being able to restrict the displacement of the fixing member.

A fluid control device according to a third embodiment of the present disclosure will be described below. The third embodiment is different from the above-described embodiments in part of configuration of the drop detector. The following description is made mainly about features of the third embodiment while components having similar configurations and substantially the same functions to those in the first and second embodiment are denoted by the same reference signs and description of those components is omitted.

As described above, the medical staff going to perform the drip ending work is needed to first close the manual clamp 102, further to operate the operation panel, for example, to release the infusion tube 101 from the state pressed by the electrical clamp 10, and then to operate the slider 17 to remove the infusion tube 101. However, if the medical staff forgets to close the manual clamp 102 in the drip ending work, there is a risk that the infusion tube 101 comes into the free flow state. Taking into account the above point, in the above-described control flow illustrated in FIG. 4, if the increase in the amount of the drops is detected in step S13, the operation of releasing the pressing on the infusion tube 101 is stopped to prevent the infusion tube 101 from coming into the free flow state.

However, the above-described control is premised on that the drip chamber 100 is in a state not removed from the drop detector 50. In other words, when the drip chamber 100 is previously removed from the drop detector 50, the increase in the amount of the drops cannot be detected, and it is difficult to prevent the infusion tube 101 from coming into the free flow state.

In consideration of the above point, the third embodiment employs a mechanism for preventing the drip chamber 100 from being removed during the drip infusion.

Figure 7:
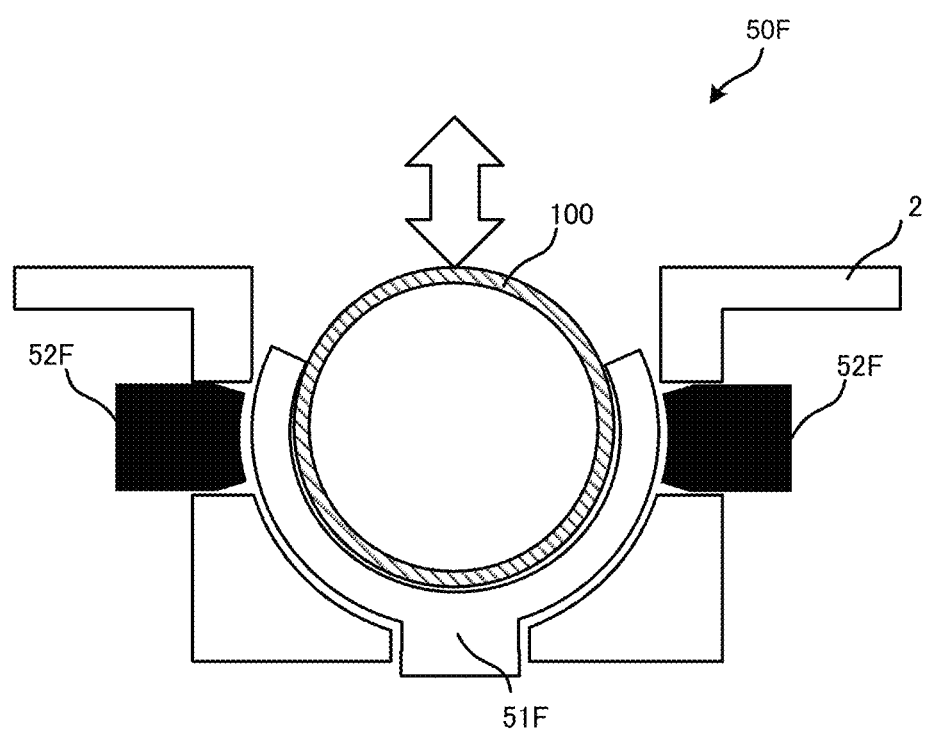
FIG. 7 is a schematic view illustrating a partial configuration of a drop detector in a third embodiment of the present disclosure.

FIG. 7 is a schematic view of a drop detector 50F.

The drop detector 50F is to hold the above-mentioned drip chamber 100 and to detect the amount of the drops with a not-illustrated optical sensor, for example. The drop detector 50F includes a drip chamber gripper 51F. The drip chamber gripper 51F is in the form of a leaf spring curved to follow the drip chamber 100, and it has a diameter comparable to or slightly smaller than that of the drip chamber 100. Thus, the drip chamber gripper 51F in the form of a leaf spring is constituted to be able to hold the drip chamber 100 between both ends thereof with both the ends deformed in swinging motions such that the drip chamber 100 can be detachably attached in place.

The drop detector 50F further includes a drip chamber stopper 52F for restricting deformation of the drip chamber gripper 51F, thereby restricting detachment of the drip chamber 100 from the drip chamber gripper 51F. The drip chamber stopper 52F is driven by the actuator 15 to be displaceable between a position where it restricts the deformation of the drip chamber gripper 51F and a position where it does not interfere with the deformation of the drip chamber gripper 51F. The drip chamber stopper 52F may be mechanically coupled to and driven by the above-mentioned actuator 15 for the electrical clamp 10, or may be driven by another actuator different from the actuator 15 for the electrical clamp 10.

In the drop detector 50F constituted as described above, the drip chamber stopper 52F is controlled in synchronism with the actuator 15 for the electrical clamp 10. More specifically, the drip chamber stopper 52F is driven by the controller 26 such that when the infusion tube 101 is pressed by the electrical clamp 10, the drip chamber stopper 52F fixedly holds the drip chamber 100 on the drip chamber gripper 51F in the casing 2, and that when the infusion tube 101 is not pressed by the electrical clamp 10, the drip chamber stopper 52F allows the drip chamber 100 to be detached from the drip chamber gripper 51F in the casing 2. With the above-described configuration, the drip chamber 100 can be prevented from being removed from the drop detector 50F before the increase in the amount of the drops is detected in the above-described step S13 in FIG. 4, and the infusion tube 101 can be more reliably prevented from coming into the free flow state.

A fluid control device according to a fourth embodiment of the present disclosure will be described below.

In the third embodiment, the drip chamber stopper 52F is driven by the actuator to be displaceable between the position where it restricts the deformation of the drip chamber gripper 51F and the position where it does not interfere with the deformation of the drip chamber gripper 51F.

However, when the drip chamber stopper 52F is mechanically coupled to and driven by the above-mentioned actuator 15 for the electrical clamp 10, a transmission mechanism is complicated and there is a possibility that the actuator 15 may be broken due to a load exerted on the actuator 15 in the case of the medical staff trying to forcedly detach the drip chamber.

Alternatively, the drip chamber stopper 52F may be driven by a second actuator different from the actuator 15 (first actuator) for the electrical clamp 10. In that case, however, the second actuator is needed. Moreover, there is a possibility that the second actuator may be broken due to a load exerted on the second actuator in the case of the medical staff trying to forcedly detach the drip chamber.

In consideration of the above point, the fourth embodiment employs a mechanism of engaging a cap 410 with an engagement portion 450.

The following description is made mainly about features of the fourth embodiment while components having similar configurations and substantially the same functions to those in the first and second embodiments are denoted by the same reference signs and description of those components is omitted.

Figure 8:
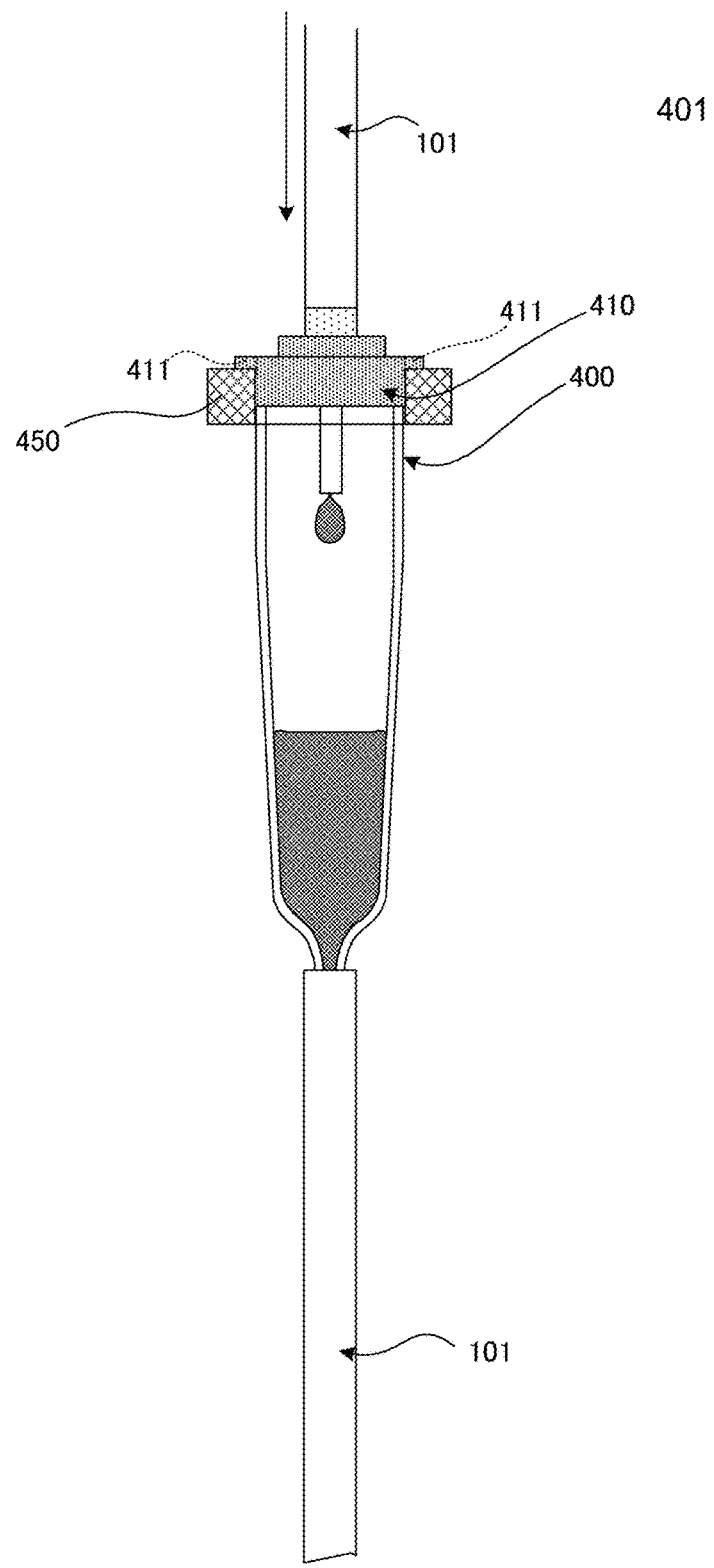
FIG. 8 is a schematic view of a fluid control device 401 according to a fourth embodiment of the present disclosure.
Figure 9:
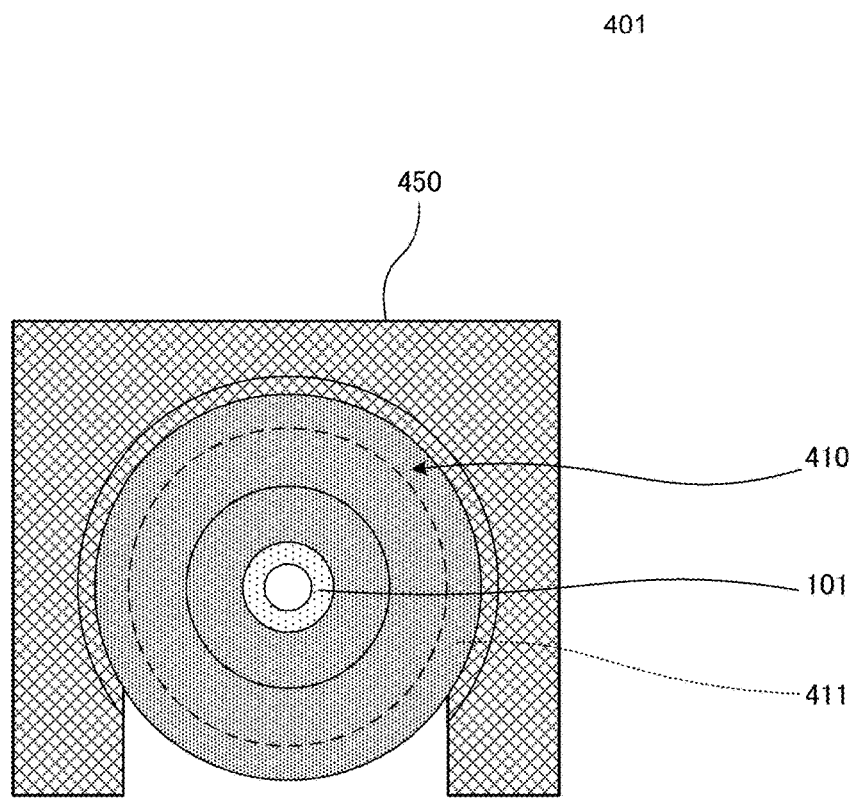
FIG. 9 is a plan view of the fluid control device 401 illustrated in FIG. 8.
Figure 10:
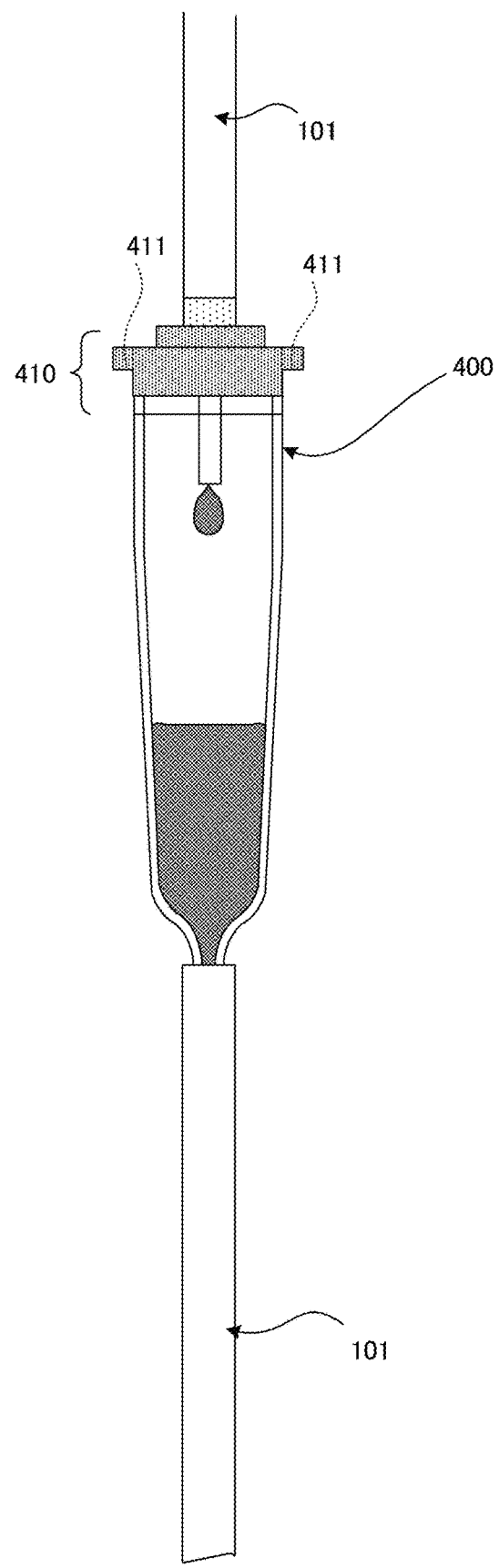
FIG. 10 is a sectional view of a drip chamber 400, an infusion tube 101, and a cap 410 illustrated in FIG. 8.
Figure 11:
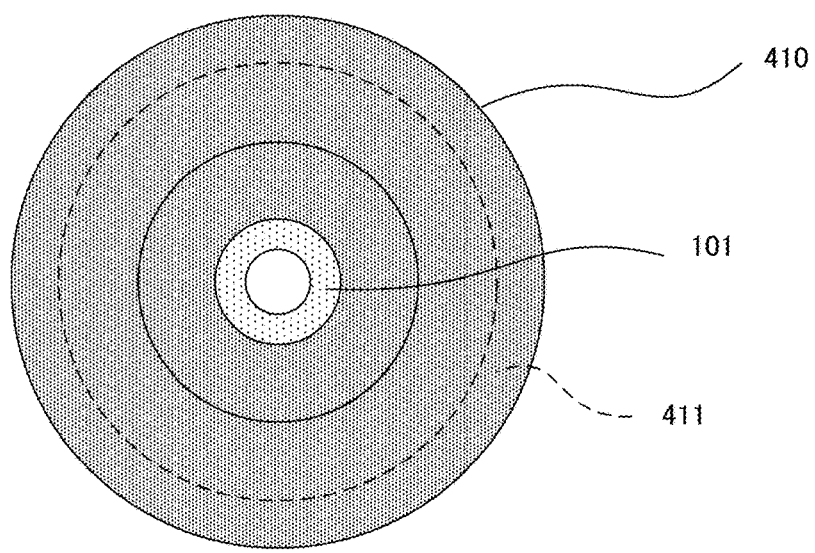
FIG. 11 is a plan view of the cap 410 illustrated in FIG. 8.
Figure 12:
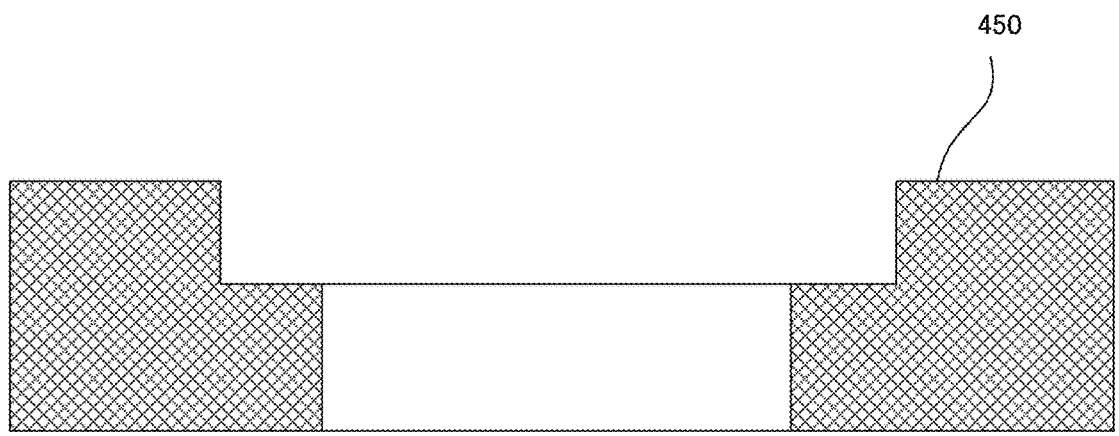
FIG. 12 is a sectional view of an engagement portion 450 illustrated in FIG. 8.
Figure 13:
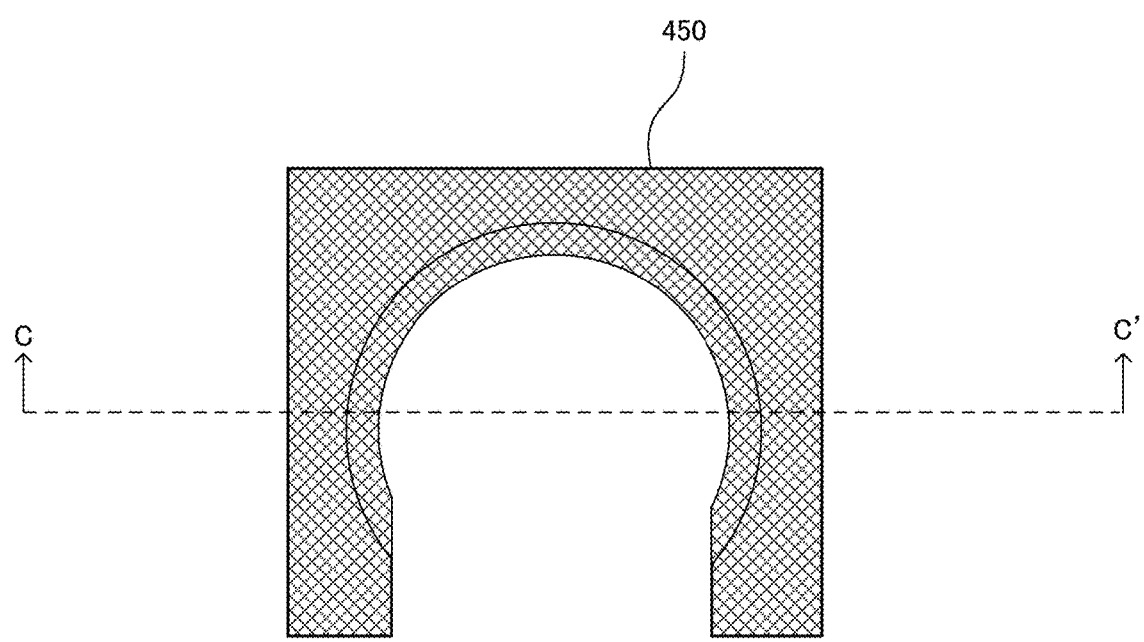
FIG. 13 is a plan view of the engagement portion 450 illustrated in FIG. 8.

FIG. 8 is a schematic view of a fluid control device 401 according to the fourth embodiment of the present disclosure. FIG. 9 is a plan view of the fluid control device 401 illustrated in FIG. 8. FIG. 10 is a sectional view of a drip chamber 400, the infusion tube 101, and the cap 410 illustrated in FIG. 8. FIG. 11 is a plan view of the cap 410 illustrated in FIG. 8. FIG. 12 is a sectional view of an engagement portion 450 illustrated in FIG. 8. FIG. 13 is a plan view of the engagement portion 450 illustrated in FIG. 8. FIG. 12 is a sectional view taken along a line C-C' in FIG. 13.

FIGS. 8 and 9 illustrate a state after the cap 410 has been engaged with the engagement portion 450. On the other hand, FIGS. 10 and 11 illustrate a state before the cap 410 is engaged with the engagement portion 450. An arrow in FIG. 8 denotes a direction in which the cap 410 is engaged with the engagement portion 450 (i.e., an axial direction of the drip chamber 400).

The fluid control device 401 includes the tube insertion portion 24 which is formed in the casing 2 and into which the drip chamber 400 is inserted in a direction substantially perpendicular to the axial direction of the drip chamber 400, and the engagement portion 450 that is engaged with a flange portion 411 of the drip chamber 400 when the drip chamber 400 inserted into the tube insertion portion 24 is slid in the axial direction of the drip chamber 400. The drip chamber 400 is different from the drip chamber 100 in that the former includes the cap 410 having the flange portion 411 formed in an end portion. The engagement portion 450 is fixed to the casing 2.

The fluid control device 401 controls the flow rate of a fluid flowing through both the drip chamber 400 and the infusion tube 101 connected to the drip chamber 400.

In the fluid control device 401 described above, a position of the drip chamber 400 is determined by the engagement portion 450. Therefore, the fluid control device 401 can more reliably perform operations of capturing drops dripping in the drip chamber 400 with an optical sensor, such as a camera or a photosensor, and detecting the amount of the drops on the basis of the number and sizes of the drops. Thus, the fluid control device 401 ensures accurate and safe control.

Furthermore, in the fluid control device 401, the flange portion 411 of the drip chamber 400 is engaged with the engagement portion 450 of the casing 2. Therefore, even if the medical staff tries to remove the drip chamber 400 from the engagement portion 450 by withdrawing the drip chamber 400 in the direction substantially perpendicular to the axial direction of the drip chamber 400 during a period in which the fluid control device 401 controls the flow rate, the drip chamber 400 is in no way disengaged from the engagement portion 450. On the other hand, even if the medical staff tries to slide the drip chamber 400 in the axial direction of the drip chamber 400, the medical staff cannot slide the drip chamber 400 in the state where the infusion tube 101 coupled to the drip chamber 400 is pressed by the pressing member 16. Thus, also in that case, the drip chamber 400 is in no way disengaged from the engagement portion 450.

Accordingly, as in the third embodiment, the fluid control device 401 can more reliably prevent the infusion tube 101 from coming into the free flow state. Moreover, as in the first and second embodiments, the fluid control device 401 can reduce the risk that the infusion tube 101 is no longer pressed and the flow rate is maximized in spite of being not intended by the medical staff.

A fluid control device according to a fifth embodiment of the present disclosure will be described below.

Figure 14:
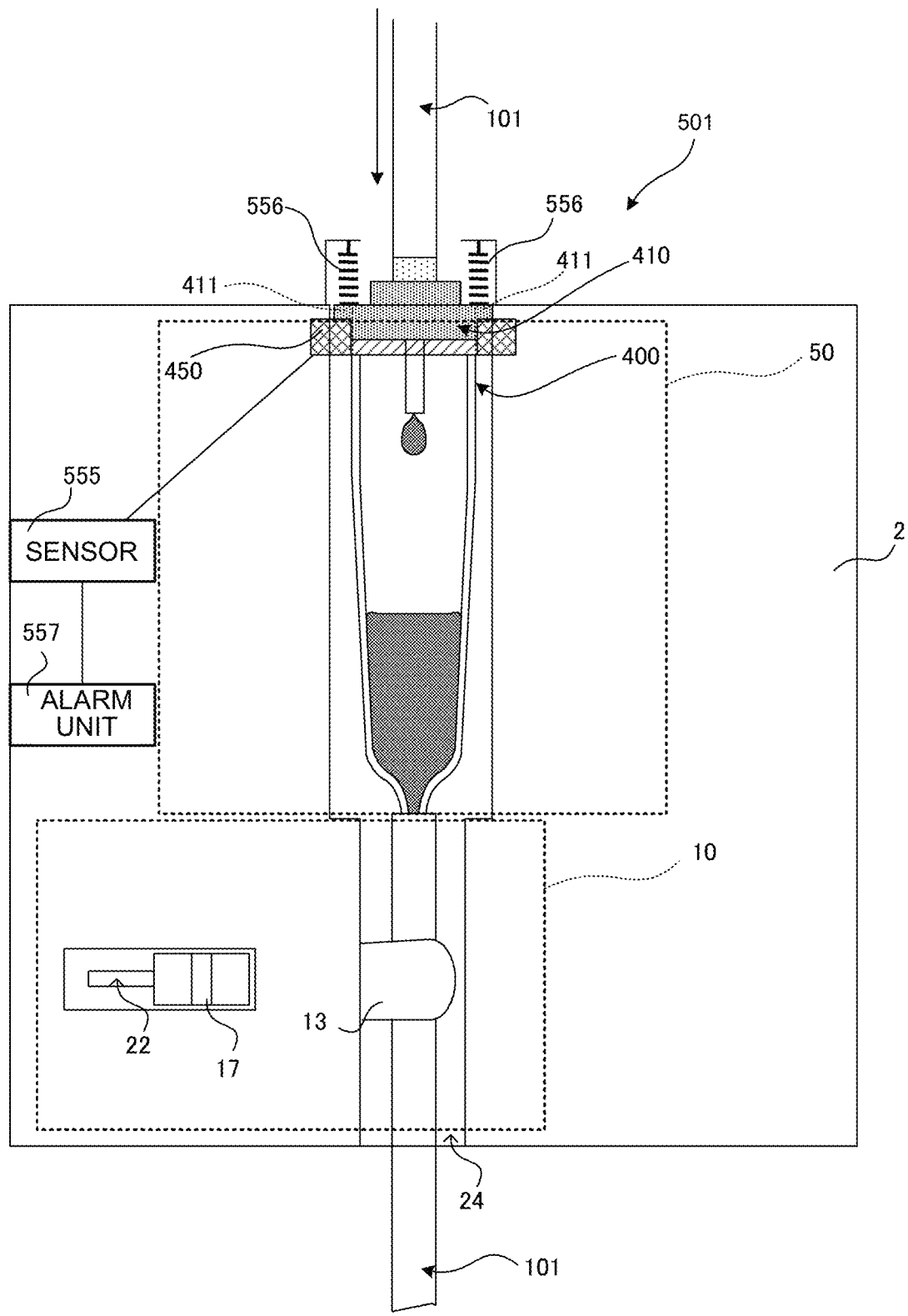
FIG. 14 is a schematic view of a fluid control device 501 according to a fifth embodiment of the present disclosure.

FIG. 14 is a schematic view of a fluid control device 501 according to the fifth embodiment of the present disclosure. The fluid control device 501 is different from the fluid control device 401 in that the former includes a spring mechanism 556, a sensor 555, and an alarm unit 557. The other configuration is the same as that of the fluid control device 401, and hence description of the other configuration is omitted.

First, the spring mechanism 556 is described in detail. The advantageous effect described in the fourth embodiment is not obtained unless, after inserting the drip chamber 400 into the tube insertion portion 24 in the direction substantially perpendicular to the axial direction of the drip chamber 400, the flange portion 411 is properly engaged with the engagement portion 450 by sliding the drip chamber 400, which has been inserted into the tube insertion portion 24, in the axial direction of the drip chamber 400.

The infusion tube 101 is coupled to the drip chamber 400. Therefore, it is not proper to expect that the drip chamber 400 is reliably engaged with the engagement portion 450 upon the drip chamber 400 falling into a cavity defined in the engagement portion 450 by gravity. It is also not proper to expect that the medical staff does not forget to slide the drip chamber 400 to be engaged with the engagement portion 450, from the intended purpose of preventing a free flow that may occur due to the event that the medical staff forgets the operation or mistakes the procedure.

From the above-described point of view, the fluid control device 501 desirably includes the spring mechanism 556 for biasing the drip chamber 400, which has been inserted into the tube insertion portion 24, to slide in the axial direction of the drip chamber 400, thus engaging the flange portion 411 with the engagement portion 450. The spring mechanism 556 is fixed, by way of example, to the casing 2.

With the provision of the spring mechanism 556, the fluid control device 501 can reduce, as in and more reliably than the first and second embodiments, the risk that the infusion tube 101 is no longer pressed and the flow rate is maximized in spite of being not intended by the medical staff.

Next, the sensor 555 is described in detail. In the above-described fluid control device 1, when the infusion tube 101 is attached to the electrical clamp 10, the infusion tube 101 is automatically pressed and closed. In other words, when the switch 20 (see FIG. 2) detects that the infusion tube 101 has been set to the fluid control device 1, the infusion tube 101 is pressed into a state closed under pressure immediately after being fixedly held in a groove.

However, if the infusion tube 101 is pressed and closed before the flange portion 411 of the drip chamber 400 inserted into the fluid control device 1 is engaged with the engagement portion 450, the flange portion 411 cannot slide to be engaged with the engagement portion 450 because the drip chamber 400 is coupled to the infusion tube 101.

Thus, from the viewpoint of preventing the free flow, the infusion tube 101 is desirably pressed into the state closed under pressure immediately after being attached to the fluid control device 1. However, it is not desirable that the infusion tube 101 is pressed into the state closed under pressure before the flange portion 411 of the drip chamber 400 is engaged with the engagement portion 450.

To cope with the above problem, the fluid control device 501 can include the sensor 555 for detecting that the flange portion 411 has been engaged with the engagement portion 450. In other words, the fluid control device 501 can automatically press the infusion tube 101 into the state closed under pressure after determining both outputs from the switch 20 for detecting the setting of the infusion tube 101 and the sensor 555 for detecting the engagement of the flange portion 411 with the engagement portion 450, and checking that the infusion tube 101 and the flange portion 411 have been both properly set.

Thus, the fluid control device 501 can reduce, as in and more reliably than the first and second embodiments, the risk that the infusion tube 101 is no longer pressed and the flow rate is maximized in spite of being not intended by the medical staff. In addition, the fluid control device 501 can accurately fix a drip port at a desired position.

The sensor 555 can detect that the flange portion 411 has been properly engaged with the engagement portion 450, by capturing an image of the drip chamber 400 with a camera, for example, and by recognizing a tip end position of the dip port or a distinctive shape pattern formed near the tip end position of the dip port. In that case, power consumption during standby can be reduced by keeping the camera for capturing a moving image in a sleep mode during standby, and by starting up the camera with the detection of the setting of the infusion tube 101 by the switch 20 being a trigger. The sensor 555 may be an optical sensor or a contact sensor other than the camera.

Next, the alarm unit 557 is described in detail. If a state where the sensor 555 does not detect the engagement of the flange portion 411 with the engagement portion 450 in spite of the switch 20 detecting the setting of the infusion tube 101 lasts for a long time (several seconds), it is thought that there occurs some trouble, such as the flange portion 411 being caught with an inlet opening of the casing 2. In that state, the fluid control device 501 cannot yet automatically press and close the infusion tube 101.

If the medical staff opens the manual clamp 102 in the above state, there is a risk of causing the free flow.

To cope with the above problem, the fluid control device 501 can include the alarm unit 557 that issues warning sounds upon detecting the above-mentioned state. The alarm unit 557 is constituted by a loudspeaker, for example. With the provision of the alarm unit 557, the fluid control device 501 can issue the warning sounds from the alarm unit 557 and notify the occurrence of some trouble to the medical staff.

The above-described embodiments are to be considered as not restrictive, but illustrative in all respects. The scope of the present invention is defined not in the above description, but in Claims. Modifications equivalent to the meaning of Claims and falling within the scope defined in Claims are all included in the present invention.

REFERENCE SIGNS LIST

A . . . tube fixing position
B . . . tube attaching/detaching position
1, 401, 501 . . . fluid control device
2 . . . casing
10 . . . electrical clamp
13 . . . lever
14 . . . coil spring
15 . . . actuator
16 . . . pressing member
17 . . . slider
18 . . . tension spring
19 . . . roller
20 . . . switch
21, 22 . . . opening
23 . . . casing chamber
24 . . . tube insertion portion
25 . . . stopper
26 . . . controller
50 . . . drop detector
100, 400 . . . drip chamber
101 . . . infusion tube
102 . . . manual clamp

The invention claimed is:

1. A fluid control device comprising:
a tube insertion portion provided in a casing;
a fixing member that fixedly holds, in the tube insertion portion, a tube inserted into the tube insertion portion, wherein the fixing member is displaced between a tube fixing position at which the fixing member fixedly holds the tube in the tube insertion portion and a tube attaching/detaching position at which the fixing member allows the tube to be attached to and detached from the tube insertion portion;
a pressing member driven by an actuator to press the tube within the tube insertion portion, wherein the pressing member maintains the fixing member at the tube fixing position at least during a period in which the pressing member presses the tube; and
a controller that controls the actuator that drives the pressing member,
wherein the controller controls the pressing member to start pressing on the tube after the fixing member fixedly holds the tube in the tube insertion portion.

2. The fluid control device according to claim 1, further comprising an operating member that receives an operation of displacing the fixing member from the tube fixing position to the tube attaching/detaching position; and
a first resilient member that applies resilient force acting on the fixing member to displace the fixing member from the tube attaching/detaching position to the tube fixing position.

3. The fluid control device according to claim 2, further comprising a drip unit in which a fluid flowing through the tube inserted into the tube insertion portion drips as drops; and
a drop detector that detects an amount of the drops dripping in the drip unit,
wherein the controller intensifies or resumes the pressing on the tube by the pressing member in fluid control ending work, when the amount of the drops detected by the drop detector increases, during an operation of reducing the pressing on the tube by the pressing member, or after the pressing member and the tube have been moved away from each other.

4. The fluid control device according to claim 2, wherein the casing includes a rolling element disposed at a position opposing to the fixing member with a passage through which the tube is inserted into the tube insertion portion in-between the rolling element and the fixing member.

5. The fluid control device according to claim 2claim 1, further comprising a second resilient member that applies resilient force acting on the operating member and the fixing member to attract both the members to each other.

6. The fluid control device according to claim 5, further comprising a drip unit in which a fluid flowing through the tube inserted into the tube insertion portion drips as drops; and
a drop detector that detects an amount of the drops dripping in the drip unit,
wherein the controller intensifies or resumes the pressing on the tube by the pressing member in fluid control ending work, when the amount of the drops detected by the drop detector increases, during an operation of reducing the pressing on the tube by the pressing member, or after the pressing member and the tube have been moved away from each other.

7. The fluid control device according to claim 5, wherein the casing includes a rolling element disposed at a position opposing to the fixing member with a passage through which the tube is inserted into the tube insertion portion in-between the rolling element and the fixing member.

8. The fluid control device according to claim 1, further comprising a drip unit in which a fluid flowing through the tube inserted into the tube insertion portion drips as drops; and
a drop detector that detects an amount of the drops dripping in the drip unit,
wherein the controller intensifies or resumes the pressing on the tube by the pressing member in fluid control ending work, when the amount of the drops detected by the drop detector increases, during an operation of reducing the pressing on the tube by the pressing member, or after the pressing member and the tube have been moved away from each other.

9. The fluid control device according to claim 8, wherein the casing includes a rolling element disposed at a position opposing to the fixing member with a passage through which the tube is inserted into the tube insertion portion in-between the rolling element and the fixing member.

10. The fluid control device according to claim 1, wherein the casing includes a rolling element disposed at a position opposing to the fixing member with a passage through which the tube is inserted into the tube insertion portion in-between the rolling element and the fixing member.

11. The fluid control device according to claim 2, further comprising a second resilient member that applies resilient force acting on the operating member and the fixing member to attract both the members to each other.

12. The fluid control device according to claim 1, further comprising a drip unit in which a fluid flowing through the tube inserted into the tube insertion portion drips as drops; and
a drop detector that detects an amount of the drops dripping in the drip unit,
wherein the controller intensifies or resumes the pressing on the tube by the pressing member in fluid control ending work, when the amount of the drops detected by the drop detector increases, during an operation of reducing the pressing on the tube by the pressing member, or after the pressing member and the tube have been moved away from each other.

13. The fluid control device according to claim 1, wherein the casing includes a rolling element disposed at a position opposing to the fixing member with a passage through which the tube is inserted into the tube insertion portion in-between the rolling element and the fixing member.

14. A fluid control device comprising:
a casing;
a tube insertion portion provided in the casing, the tube insertion portion having an opening to insert a tube into the tube insertion portion;
a fixing member, one end of the fixing member being pivotally supported for opening and closing the opening to the tube insertion portion, wherein when the fixing member pivots to close the opening of the tube insertion portion, the tube is kept inside the tube insertion portion;
a pressing member provided in the casing, the pressing member being farther away from the opening than the fixing member, the pressing member configured for protruding and pressing the tube within the tube insertion portion, the pressing member comprising a stopper that collides with other end of the fixing member, the stopper prevents the opening of the tube fixing position from being opened at least during a period in which the pressing member presses the tube;
an actuator connected to the pressing member; and
a controller connected to the actuator, the controller controlling the actuator to drive the pressing member,
wherein the controller controls the pressing member to start pressing on the tube after the fixing member fixedly holds the tube inside the tube insertion portion.

15. The fluid control device according to claim 14, further comprising an operating member that is connected to the fixing member, when the operating member receives an operation of displacing the fixing member from the tube fixing position to the tube attaching/detaching position, the operating member pulls the fixing member to open the opening of the tube insertion portion; and
a first resilient member provided at the one end of the fixing member, the first resilient member applying resilient force acting on the fixing member to displace the fixing member from the tube attaching/detaching position to the tube fixing position.

16. The fluid control device according to claim 14, further comprising a second resilient member that connects the operating member and the fixing member, the second resilient member applying resilient force acting on the operating member and the fixing member to attract both of the members to each other.

17. The fluid control device according to claim 14, further comprising a drip unit connected to the tube between an end of the tube and the fluid control device, in the drip unit, a fluid flowing through the tube inserted into the tube insertion portion dripping as drops; and
a drop detector to which the drip unit is attached, the drop detector detects an amount of the drops dripping in the drip unit,
wherein the controller intensifies or resumes the pressing on the tube by the pressing member in fluid control ending work, when the amount of the drops detected by the drop detector increases, during an operation of reducing the pressing on the tube by the pressing member, or after the pressing member and the tube have been moved away from each other.

18. A fluid control device comprising:
a tube insertion portion provided in a casing;

a fixing member that fixedly holds, in the tube insertion portion, a tube inserted into the tube insertion portion;

a pressing member driven by an actuator to press the tube within the tube insertion portion; and a controller that controls the actuator that drives the pressing member, wherein the controller controls the pressing member to start pressing on the tube after the fixing member fixedly holds the tube in the tube insertion portion, and wherein the casing includes a rolling element disposed at a position opposing to the fixing member with a passage through which the tube is inserted into the tube insertion portion in-between the rolling element and the fixing member.

\* \* \* \* \*